(12) United States Patent
Kandel et al.

(10) Patent No.: US 8,908,175 B1
(45) Date of Patent: Dec. 9, 2014

(54) FLEXIBLE SCATTEROMETRY METROLOGY SYSTEM AND METHOD

(75) Inventors: Daniel Kandel, Aseret (IL); Michael Adel, Zichron Ya'akov (IL); Joel Seligson, Misgav (IL); Boris Golovanevsky, Haifa (IL)

(73) Assignee: KLA-Tencor Corporation, Milpitas, CA (US)

( * ) Notice: Subject to any disclaimer, the term of this patent is extended or adjusted under 35 U.S.C. 154(b) by 268 days.

(21) Appl. No.: 11/521,118

(22) Filed: Sep. 13, 2006

Related U.S. Application Data

(60) Provisional application No. 60/787,784, filed on Mar. 31, 2006.

(51) Int. Cl.
*G01N 21/00* (2006.01)

(52) U.S. Cl.
USPC ......... 356/323; 356/317; 356/237.4; 356/625

(58) Field of Classification Search
USPC .......................................... 356/625, 337, 341
See application file for complete search history.

(56) References Cited

U.S. PATENT DOCUMENTS

| | | | |
|---|---|---|---|
| 5,392,094 A * | 2/1995 | Kudo | 355/67 |
| 5,717,518 A | 2/1998 | Shafer et al. | |
| 5,943,170 A * | 8/1999 | Inbar et al. | 359/561 |
| 6,075,565 A | 6/2000 | Tanaka et al. | |
| 6,338,819 B1 | 1/2002 | Braga et al. | |
| 6,560,039 B1 | 5/2003 | Webb et al. | |
| 6,798,511 B1 * | 9/2004 | Zhan et al. | 356/369 |
| 7,141,802 B2 * | 11/2006 | Takeyama et al. | 250/458.1 |
| 7,193,774 B2 * | 3/2007 | Cheng et al. | 359/386 |
| 7,317,531 B2 | 1/2008 | Mieher et al. | |
| 2002/0191281 A1 * | 12/2002 | Osa et al. | 359/385 |
| 2004/0033426 A1 * | 2/2004 | Den Boef et al. | 430/22 |
| 2004/0125373 A1 * | 7/2004 | Oldenbourg et al. | 356/364 |
| 2004/0233441 A1 | 11/2004 | Mieher et al. | |
| 2005/0046855 A1 * | 3/2005 | Davidson | 356/451 |
| 2005/0134687 A1 * | 6/2005 | Kaminsky et al. | 348/169 |
| 2006/0098195 A1 * | 5/2006 | Brill et al. | 356/326 |

\* cited by examiner

*Primary Examiner* — Tarifur Chowdhury
*Assistant Examiner* — Rebecca C Bryant
(74) *Attorney, Agent, or Firm* — Suiter Swantz pc llo

(57) ABSTRACT

A scatterometry tool including an illumination source for directing a light beam into a first optical beam shaping and positioning element at an illumination pupil plane of the tool where the light beam is modulated and directed to an objective lens system having a high numerical aperture. The objective receiving the modulated light beam and directing it onto a target to generate a scattering signal. The objective lens collects the scattering signal and directs it to a second optical beam shaping and positioning element at a collection pupil plane where the signal is modulated and then directed to detectors for receiving and processing the signal to determine surface characteristics of the target.

36 Claims, 5 Drawing Sheets

FLEXIBLE SCATTEROMETRY METROLOGY SYSTEM AND METHOD

CROSS REFERENCE TO RELATED PATENT APPLICATIONS

This application is related to and claims priority to Application No. 60/787,784, filed Mar. 31, 2006, entitled "FLEXIBLE SCATTEROMETRY INSPECTION SYSTEM AND METHOD", by Daniel Kandel, et al. The above application being incorporated by reference in its entirety for all purposes.

Also, this application is related to the following U.S. Provisional Patent Applications:
(1) Application No. 60/431,314, entitled METHOD FOR DETERMINING OVERLAY ERROR BY COMPARISON BETWEEN SCATTEROMETRY SIGNALS FROM MULTIPLE OVERLAY MEASUREMENT TARGETS, by Walter D. Mieher et al., filed 5 Dec. 2002,
(2) Application No. 60/440,970, entitled METHOD FOR DETERMINING OVERLAY ERROR BY COMPARISON BETWEEN SCATTEROMETRY SIGNALS FROM MULTIPLE OVERLAY MEASUREMENT TARGETS WITH SPECTROSCOPIC IMAGING OR SPECTROSCOPIC SCANNING, by Walter D. Mieher, filed 17 Jan. 2003,
(3) Application No. 60/504,093, entitled APPARATUS AND METHODS FOR DETECTING OVERLAY ERRORS USING SCATTEROMETRY, by Walter D. Mieher, filed 19 Sep. 2003,
(4) Application No. 60/449,496, entitled METHOD AND SYSTEM FOR DETERMINING OVERLAY ERRORS BASED ON SCATTEROMETRY SIGNALS ACQUIRED FROM MULTIPLE OVERLAY MEASUREMENT PATTERNS, by Walter D. Mieher, filed 22 Feb. 2003,
(5) Application No. 60/498,524, filed 27 Aug. 2003, entitled "METHOD AND APPARATUS COMBINING IMAGING AND SCATTEROMETRY FOR OVERLAY METROLOGY", by Mike Adel, and
(6) Application No. 60/785,430, filed 23 Feb. 2004, entitled "APPARATUS AND METHOD FOR DETECTING OVERLAY ERRORS USING SCATTEROMETRY", and published as Application No. 20040233441 on 25 Nov. 2004, by Walter D. Mieher, et al. These applications are herein incorporated by reference in their entirety.

TECHNICAL FIELD

The invention described herein relates generally to surface metrology and testing. In particular, the invention relates to testing apparatus and methods for implementing an apparatus capable of executing a wide range of scatterometry and/or imaging testing, all on the same test platform.

DISCLOSURE

For many years, scatterometry methodologies have been used to inspect surfaces. Many of these methods make use of light scattered or diffracted by the surface to characterize and examine features of the surface. As used herein, scattered light shall refer to both scattered light and diffracted light.

Many different types of scatterometry apparatuses have been constructed to conduct different types of scatterometry measurements in order to characterize inspection surfaces. Each type of testing examines different parameters and requires different types of equipments. The inventors seek to construct a single apparatus capable of conducting many different types of scatterometry measurements using the same inspection apparatus.

As is known to those having ordinary skill in the art, each of the different types of scatterometry measurements requires different scattering parameters in order to obtain the desired information. Parameters such as angle of incidence (AOI), azimuth angle, illumination numerical aperture (illumination NA), collection numerical aperture (collection NA) and the diffraction order of the collected light can widely vary for each type of scatterometry measurement taken. Additionally, these parameters can radically vary depending on the type of metrology application desired. The variance is so much that separate devices are generally employed to capture measurements for each different type of metrology application.

Scatterometry has become an important technology with several valuable metrology applications in the semiconductor industry. Scatterometry applications can be used to obtain thin film (TF) and critical dimension (CD) measurements. Additionally, scatterometry has demonstrated significant potential for overlay (OVL) metrology (also referred to herein as scatterometry overlay metrology (SCOL)).

However, one limitation of existing scatterometry tools is that they are narrow in their application. In other words, due to different design specifications and limitations, a separate tool is required for each of these applications. As already hinted at, this is due to a large variance in the tool requirements for each of these scatterometry applications. Consequently, many architecturally distinct tools have been developed to meet the needs of the industry.

The following paragraphs will explain some of the variability in the existing tools and why this situation is a problem.

Thin film (TF) metrology is used to make determinations about the properties of generally featureless films (one example of such a film can be a dielectric material layer). Such TF metrology using scatterometry requires a very large angle of incidence (AOI) (about 70°) and small collection numerical aperture (NA), e.g., 0.04, to achieve the required sensitivity. As used here, and as generally known in the art, the AOI is the angle of incidence for a light beam as measured from a line normal to a target surface. TF metrology is also insensitive to the azimuth angle of the measurement, although the presence of underlying structures can change this. As used here, and as generally known in the art, the azimuth angle for an incident light beam is measured in degrees of rotation about a line normal to the target surface. Due to the relative insensitivity of TF metrology to variations in azimuth angle, TF scatterometry tools can employ R-theta stages rather than x-y stages, which may be necessary for certain integrated applications.

Critical dimension (CD) metrology is used to make determinations about the properties of features formed in film layers. Commonly, this means features formed in a single layer of the target under inspection. CD metrology typically requires a fairly large AOI for sensitivity, but has slightly more flexibility in this parameter than is the case for TF measurements. Thus, it can be advantageous to use a smaller AOI (e.g., 60°) in order to reduce the spot size and thus the size of the target. However, unlike TF metrology, CD measurements are sensitive to the azimuth angle, and azimuth control can provide certain advantages and lead to improved sensitivity. In addition to the above limitations, the dependence of CD scatterometry measurements on azimuth angle prevents the use of an R-theta stage with most currently used spectroscopic ellipsometry-based (SE) scatterometry architectures. Thus, most current CD metrology tools do not employ R-theta stages.

In scatterometry overlay (SCOL), the drive to reduce target size is much stronger than in either TF or CD applications, since the currently dominant technology (imaging overlay) is capable of measuring targets as small as 15×15 µm² (micrometer squared). Therefore it is advantageous for SCOL to use a small AOI (commonly in the range of 20°-30°) even at the price of a somewhat inferior sensitivity. Additionally, SCOL metrology can benefit from on-the-fly (changeable during the inspection process) azimuth control for improved sensitivity. In addition, SCOL measurements typically use a larger NA (e.g., 0.2) than is used for other more standard scatterometry applications in order to reduce spot size.

SCOL and also other scatterometry applications may also benefit from a one-dimensional spectral imaging capability. Such a capability, when applied to a SCOL application, has the potential of significantly reducing MAM time (move-acquire-measure time) and target size.

Commonly, current scatterometry applications use the zero-order reflected light. The inventors contemplate, that future applications can take advantage signal having higher diffraction orders. Thus, the inventors have created (and disclosed herein) a device capable of flexible azimuth and angle of collection (AOC) control on the collection side that enables the selective detection of different diffraction orders of light for each measurement.

The inventors have invented a scatterometry apparatus that is fairly simply constructed and yet offers extreme flexibility. This single tool is able to perform TF, CD and OVL metrology using the same tool instead of separate tools as heretofore required. The inventive tool is able to conduct TF, CD and OVL metrology measurements at their respective optimal angles of incidence, azimuth angles, and numerical apertures. Moreover, the inventive tool enables diffraction order selection. Also, the inventive tool can be employed using an R-theta stage for integratability as well as 1D spectral imaging.

These and other inventive aspects of the invention will be discussed hereinbelow.

SUMMARY OF THE INVENTION

In accordance with the principles of the present invention, flexible scatterometry tools and methodologies are disclosed.

Numerous aspects of the present invention are described in detail in the following description and drawings set forth hereinbelow.

In one embodiment, the invention teaches as a scatterometry apparatus capable of flexible modes of operation. Such an apparatus includes an illumination source; a first optical beam shaping and positioning element; a high numerical aperture objective lens system; a detector for measuring a light scattering signal; and a control element. The combination of elements arranged such that the light from the illumination source is shaped into at least one illumination beam by the first optical beam shaping and positioning element and such that the at least one illumination beam passes through the high numerical aperture objective lens system to impinge on a target site which generates a light scattering signal collected, in turn, by the objective lens system. After passing through the objective the scattering signal is received by the detector where scatterometry measurements are made.

In another embodiment, a second optical beam shaping and positioning element is arranged in an optical path between the high numerical aperture objective lens system and the detector and configured to selectively modulate the light scattering signal from the high numerical aperture objective lens system.

In another embodiment, the first optical beam shaping and positioning element is configured to alter illumination parameters for metrology measurements. Such parameters include, but are not limited to angle of incidence, illumination azimuth, illumination numerical aperture, illumination symmetry, illumination beam shape and other parameters.

In another embodiment, the second optical beam shaping and positioning element is configured to alter collection parameters for metrology measurements. Such parameters include, but are not limited to, angle of collection, collection azimuth, collection numerical aperture, collection diffraction order, collection symmetry, dark field and light field mode of operation, and other parameters.

In a method embodiment, the invention involves illuminating a first optical beam shaping and positioning element arranged at an illumination pupil plane of the apparatus so that a modulated illumination beam passes through the element and directing the modulated illumination beam through a high numerical aperture objective lens system and onto a target where the target topology generates a light scattering signal. The first optical beam shaping and positioning element is configured to adjust optical parameters of the modulated illumination beam with the first optical beam shaping and positioning element. A portion of the light scattering signal is collected using the high numerical aperture objective lens the is directed in an optical path where it is received by a second optical beam shaping and positioning element arranged at a collection pupil plane of the apparatus. The second optical beam shaping and positioning element configured to enable adjustment of optical parameters of scattering signal to form a modulated signal. The modulated signal is received by detectors capable of analyzing the modulated signal. The detected signal is then analyzed.

BRIEF DESCRIPTION OF THE DRAWINGS

The following detailed description will be more readily understood in conjunction with the accompanying drawings, in which.

It is to be understood that, in the drawings, like reference numerals designate like structural elements. Also, it is understood that the depictions in the Figures are not necessarily to scale.

DESCRIPTION OF SPECIFIC EMBODIMENTS

The present invention has been particularly shown and described with respect to certain embodiments and specific features thereof. The embodiments set forth herein below are to be taken as illustrative rather than limiting. It should be readily apparent to those of ordinary skill in the art that various changes and modifications in form and detail may be made without departing from the spirit and scope of the invention.

The following detailed description describes various embodiments of flexible multi-purpose scatterometry tools and methods for their use. Unlike commonly employed ellipsometry systems, which generally employ illumination beams that are not normal to the target surface and collection angles configured to receive signal from the target surface at non-normal angles, the present invention uses a different architecture. The inventors have conceived of a device architecture configured in an imaging-like design. In other words the optical axis is normal (or nearly normal) to the target surface. Additionally, a high numerical aperture (NA) objective lens system is employed. Such lenses are employed in many other applications but have not found use in SCOL devices or other scatterometry applications. Examples, of such high NA objective lens systems can include, but are not limited to, objectives such as are described U.S. Pat. Nos. 6,388,819, 6,075,565 and so on. The NA of the inventive objective lens system should be large enough to include the full required range of prospective AOI's. For example, an objective of NA 0.9 includes all AOI's less than 64°, while NA of 0.94 includes all AOI's less than about 70°. In one example implementation an objective with an NA of 0.94 is employed.

To select the desired AOI, angle of collection and the illumination and collection azimuth and NA, the optics are designed so that pupils are imaged onto a desired plane in the illumination path and onto a desired plane in the collection path. In one example embodiment, a pupil can be arranged in the back focal plane of the objective lens system used for the device. This can be done either by adding relay optics to image the pupil, or by designing the objective so that images of the pupil are located in the desired positions. The inventors can arrange the pupil plane so that position in the pupil plane corresponds to angle in the field. To be specific, the R coordinate in the pupil plane corresponds to AOI or angle of collection in the field, and the theta coordinate in the pupil plane corresponds to the azimuth angle in the field.

Figure 1A:
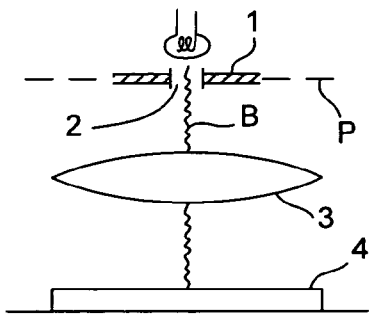
FIGS. 1(a)-1(c) are simplified schematic views of an adjustable optical beam shaping and positioning element and its relationship with an associated objective in one embodiment constructed in accordance with the principles of the invention.
Figure 1B:
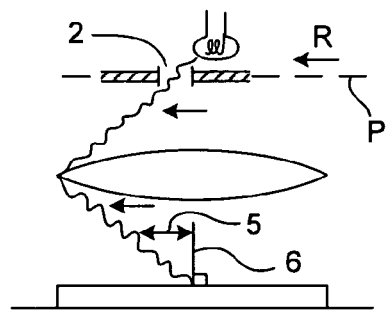
Figure 1C:
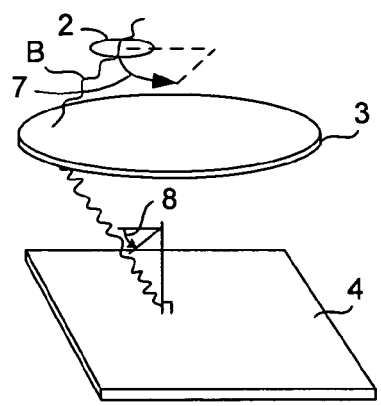

This feature is described in the simplified schematic drawing FIGS. 1(a)-1(c) which are described as follows. FIGS. 1(a)-(c) depict but one embodiment of a general principle to which one of ordinary skill can configure many adaptations in accordance with the principles of the invention. By installing an adjustable optical beam shaping and positioning element in the illumination pupil plane the angle of incidence and azimuth can be varied at will during an inspection or measurement process. FIGS. 1(a)-1(c) provide a simplified depiction of this process. For example, in FIG. 1(a) an adjustable optical beam shaping and positioning element 1 is positioned in an illumination pupil plane. One such pupil plane P can be the back focal plane of the objective lens system (schematically depicted here in simplified form as lens system 3). In this simplified embodiment, the optical beam shaping and positioning element 1 features a single movable hole 2 arranged with respect to an objective lens element 3 such that an optical beam B passes through the hole 2 an forms an illumination spot S on a target 4. As will be apparent to those of ordinary skill the hole can be of many sizes and shape and can be created using mechanically or, alternatively, using diffractive or other optical elements. Other aspects of the optical beam shaping and positioning element 1 will be discussed in greater detail hereinbelow. Continuing, by moving the hole 2 (i.e., adjusting the R component as shown in FIG. 1(b)) the position of the beam (and hence the position of the spot S1') can be moved over the surface of the target and in some embodiments, the angle of incidence 5 can also be varied. Additionally, by moving the hole 2 radially 7 about a line normal 6 to the inspection plane the azimuth angle 8 for the incident illumination beam can be readily adjusted.

The adjustable optical beam shaping and positioning element is placed in a pupil plane and is capable of adjusting the size, shape, and position of an illumination aperture used to regulate the illumination beam. This mechanism for adjusting the pupil enables the user to select any desired position in the illumination pupil plane. A similar adjustable optical beam shaping and positioning element is placed in the collection pupil plane and is capable of adjusting the size, shape, and position of a collection aperture used to regulate the collected beam (e.g., the angle of collection, the azimuth and the NA of the collected light). Moreover, the mechanism can be is configured so that an adjustment in the illumination pupil plane is independent from adjustments made in the collection pupil plane. The inventors contemplate that this can be done in a number of different ways. Additionally, the switching between different illumination and collection patterns in the pupil planes can be done on a per measurement basis and also on-the-fly (i.e., at any point during an in-process metrology cycle) during measurements if desired. Hence, the invention enables different scatterometry applications to be done with the same tool without the need for separate tools for each type of measurement.

Some example embodiments are described with respect to the following Figures which are described in detail in the following paragraphs.

Figure 1D:
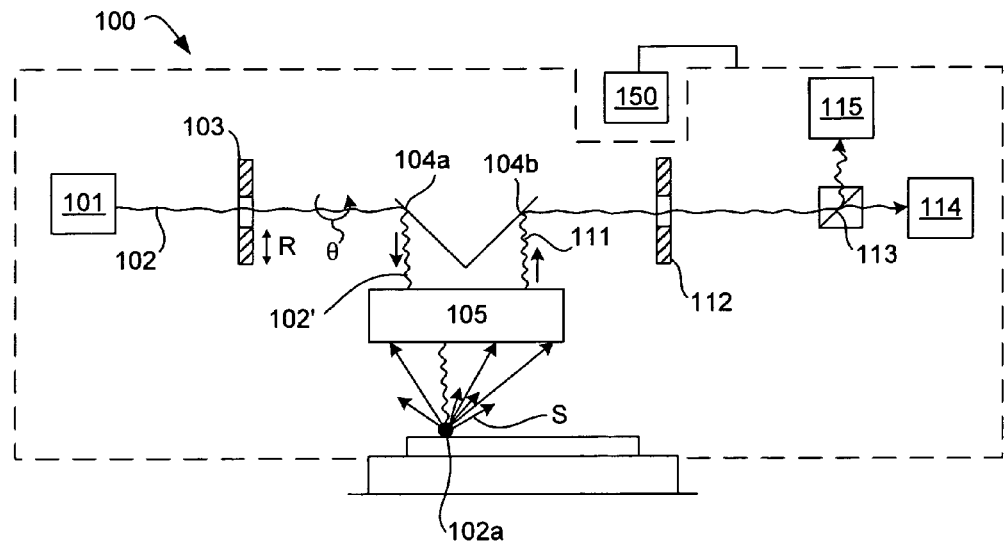
FIG. 1(d) is a simplified schematic cross-sectional view of a flexible scatterometry apparatus embodiment constructed in accordance with the principles of the invention.

FIG. 1(d) is a simplified schematic depiction of one particular embodiment of a device constructed in accordance with the principles of the invention. This example architecture provides a simplified illustration of a tool 100 which can be employed in wide range of ellipsometry application including, for example, very broad-band (e.g., 150-1000 nm) ellipsometry applications requiring a relatively high degree of spectral fidelity.

The depicted apparatus includes an illumination source 101 configured to pass a light beam 102 through an optical beam shaping and positioning element 103 and direct the beam through a high NA optical element 105 and onto a metrology target 106 where light scattering occurs. The high NA optical element 105 collects the scattered light which passes through a second optical beam shaping and positioning element 112 (arranged in a collection pupil plane) that directs the collected light 111 onto detection and analysis systems 114, 115.

The following is a more detailed description of the elements depicted in the embodiment of FIG. 1(d). An illumination source 101 is positioned so that it is capable of illuminating a target 106. Although shown here as set to one side, in practice, the light source can be employed in any suitable optical arrangement. Commonly, broadband illumination sources (e.g., a halogen light source or an arc lamp) are employed. Such sources can be filtered or polarized as needed. Alternative embodiments can employ monochromatic sources such as lasers.

In the depicted arrangement, the illumination source 101 has been positioned off to a side of the device 100 with reflective elements arranged to direct the light beam down to the target. As mentioned above, the depicted arrangement is just one particular embodiment with many other arrangements being possible (for example the light source could be positioned directly above the inspection point). The source 101 generates a light beam 102 which is directed through an optical beam shaping and positioning element 103 and then onto an objective system 105 and onto the target surface 106 where spot of light 102a is formed and a scattering pattern S is generated.

A first optical beam shaping and positioning element 103 is arranged in an illumination pupil plane of the device 100. The optical beam shaping and positioning element 103 regulates the position, shape, and size of an input light beam. In one approach, the optical beam shaping and positioning element 103 can comprise a rotating or sliding set of apertures having desired patterns. For example, the patterns can be used to adjust the size, shape, and position of the apertures through which the light 102 passes. Alternatively, a fixed size pupil can be moved to various predetermined positions in the pupil plane. The previously explained R and theta offsets can be used to regulate the AOI and azimuth angles. For example, in one embodiment a pupil 103 can be offset in a direction R and rotated θ about an axis to obtain AOI and azimuth angle variations. In one implementation, the optical beam shaping and positioning element 103 can comprise a rotary wheel having a family of different sized and shaped apertures set at differing R distances which can be rotated to the desired azimuth settings as needed by the user to set the illumination settings.

In one particularly elegant approach, the optical beam shaping and positioning element 103 can comprise one or more spatial light modulators placed in the pupil plane (e.g., the back focal plane of the objective 105). Such modulators comprise a class of devices having a mass of addressable pixels that can be selectively activated or deactivated to influence the light pattern of light impinging on the modulator. Generally, such spatial light modulators (SLM's) are divided into small pixels that can be controllably activated or deactivated. The transmission (or reflection) of each pixel can be adjusted in order to generate apertures of arbitrary size, shape, and position to adjust the spatial pattern of the light passing through the modulator. This can allow very fast and accurate tuning of their spatial pattern.

SLM's can be constructed in a number of different arrangements and configurations and operate according to a number of different principles. For example, one type of SLM comprises an array individually addressable micromirrrors that can be operated to alter the light pattern of light directed onto the SLM. This MEMS technology is widely available. For example, Texas Instruments, of Dallas Tex. produces arrays of deformable mirror devices as a "DLP" technology. Although such technologies are known, they have never been used in such applications as described here. Another approach uses arrays of optically addressable pixels that can be made selectively opaque or transmissive. For example, arrays of liquid crystal devices can be used in this way. Also, electronically addressable array elements effecting phase or amplitude modulation can be employed. One example of a suitable SLM device can be the HEX-127 SLM optically transformable mask made by Meadowlark Optics of Frederick, Colo. Additionally, numerous customized SLM's of various types can be employed with various embodiments of the device. Many different types of SLM's operating as optically transformable masks having individually addressable and adjustable pixels can be suitable for various embodiments of the invention. In other implementations, diffractive optical elements can be used to image a pupil into the desired position in the pupil plane to achieve the same or similar effects to those described above.

An advantageous aspect of the depicted embodiment (of FIG. 1(*d*)) is that the illumination pupil (e.g., 103) can be configured independently (and differently) from the collection pupil (e.g., 112). For example, FIG. 1(*e*) shows a schematically depicted SLM 120 configured with 121 a simple circular pupil which can be used in a illumination or collection pupil (103, 112). An alternatively configured SLM 130 is schematically depicted in FIG. 1(*f*). The depicted SLM 130 is configured to capture an annular pattern. When arranged in the collection plan such an arrangement can collect light of selected diffraction orders and can be arranged to have a symmetric light collection pattern. When in the illumination plane, such a pattern can facilitate symmetric illumination of the target which has its own advantages. Additionally, in addition to these simple patterns, the inventors contemplate that many, many, pupil embodiments known to those having ordinary skill in the art can be easily configured with SLM's used in accordance with the principles of the invention.

Additionally, the SLM's can be used to adjust a number of other inspection parameters. For example, the SLM's (e.g., 103, 112) can be used to adjust the system NA parameters. Generally, the illumination NA can be associated with the size of the aperture, the AOI associated with the R distance, and the illumination azimuth associated with the degree of rotation about a predetermined axis. The positions of the centers of the apertures determine the AOI, and the illumination azimuth. The greater the distance R off a centerline of the objective the greater the AOI and the degree of rotation about a line normal to this centerline determines an illumination azimuth. Additionally, the size of the apertures determines the effective illumination NA's. Very wide apertures define a large illumination NA whereas a small aperture defines a smaller illumination NA. It should be noted that a symmetrical aperture patterns can facilitate symmetrical illumination patterns which are advantageous for many illumination implementations. The same can be said about the collection end where a second optical beam shaping and positioning element 112 can be adjusted in a similar fashion to vary collection NA, angle of collection, and the collection azimuth.

Returning to FIG. 1(*d*) the modulated incident beam 102' is directed into an objective lens system 105. Here that is accomplished using a reflector 104a. The important aspect is that the beam 102' is directed into the high NA objective 105. The matter of doing so is not especially crucial. Suitable types and embodiments for objective lens systems are known to those having ordinary skill in the art. Examples of some high NA objectives include but are not limited to those described in U.S. Pat. Nos. 5,717,518, 6,075,565, 6,388,819, or 6,560, 039, as well as many others. An article entitled "Small Catadioptric Microscope Optics" in "Proceedings of SPIE, Vol. No. 5523" by Shaefer, Chuang, and Armstrong discloses several approaches for constructing suitable high numerical aperture objective lens systems in accordance with the principles of the invention. Catadiopteric objectives being well suited to the principles of the invention. Refractive and reflective lens systems (as well as combinations thereof) may be employed in the objective lens system 105 in accordance with various embodiments of the invention. In the depicted embodiment, an all reflective lensing system can be used, including an objective lens system 105 comprised entirely of reflective optical elements. As stated previously, the objective 105 here is a high NA system (e.g., 0.90 or better, the exact parameters are of course adjustable and depend on the needs of the system, for example, the NA would typically be set to accommodate the maximum NA required by any aspect of the metrology system with a NA of about 0.95 being not uncommon).

The beam 102' is then directed onto the target 106 (which typically rests on a movable stage 107) where it is scattered S by the topology of the target. This scattered signal S is then collected by the large NA objective lens system 105 and directed toward the receiving instrumentation (here elements 114, 115) as a "received signal" 111. In this embodiment, the received signal 111 passes upward to a reflector 104b which directs the signal 111 to another optical beam shaping and positioning element 112 arranged in a collection pupil plane of the device. As described above, this optical modulator 112 can be a rotating or sliding set of apertures of the desired patterns or aperture sizes and positions which are introduced into the pupil plane as needed. Alternatively, a fixed size pupil can be moved to various predetermined positions in the pupil plane.

As previously explained, in one attractive alternative, the second (or collection) optical beam shaping and positioning element 112 can be a spatial light modulator placed in the pupil plane to adjust the shape, size, and position of an aperture or generally adjust the spatial pattern of light 111 passing through a modulator. Also, as before, diffractive optical elements can be used as the optical beam shaping and positioning element 112. Also, as described previously, the positions of the centers of the apertures can be used to select the AOI, angle of collection and the collection azimuth. The sizes of the apertures can also determine the effective collection NA. Additionally, different configurations of the optical beam shaping and positioning element 112 can enable different diffraction order signals to be selectively detected, since different diffraction orders are scattered at different angles.

In the depicted embodiment the modulated beam 111' is directed to detector devices (114, 115). Here that is accomplished using a reflector 113 which is movable (or alternatively some variety of beam splitter). While the reflector 113 is in place, the beam is directed to a vision navigation system 115. The vision system 115 enables the system to navigate to the desired target location. Such vision systems are known and commonly used for navigation purposes. By removing the reflector 113, the beam 111' can be directed to a spectrometer 114 for spectrographic measurements and analysis of the inspected surface. Spectrometers having suitable characteristics are widely available and can be obtained from many manufacturers. In one example, a suitable spectrometer is an Inspector Model Nos. V8, V10, N17B which can be obtained from Spectral Imaging Systems. Additionally, in place of the replaceable reflector 113 a beam splitter can be substituted enabling signal to be simultaneously directed into elements 114 and 115. The applicants further point out that control circuitry 150 is connected with the device 100 and can be used to control all operational aspects of the device 100. Examples can include the control of a stage upon which a target substrate can be placed, control of the beam shaping elements 103, 112, and all of the other controllable elements of the device 100. Such control elements are typically microprocessor controlled and comprise a wide range of control elements known to those having ordinary skill in the art.

Figure 1E:
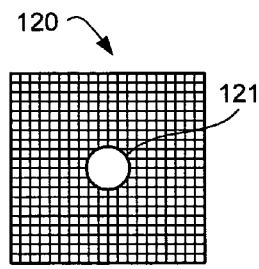
FIGS. 1(e)-1(g) are simplified views of one particular embodiment of a spatial light modulator arranged in specific configurations in accordance with the principles of the invention.
Figure 1F:
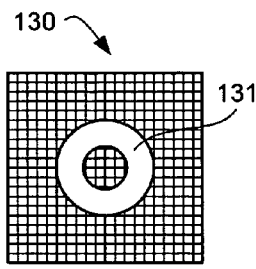
Figure 1G:
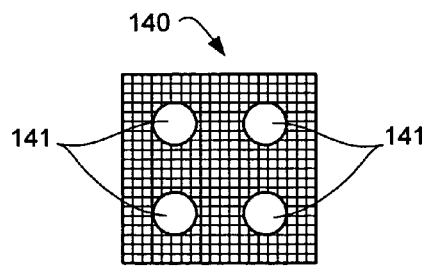

FIGS. 1(e)-1(g) schematically illustrate a few SLM configurations that are suitable for enabling certain aspects of the invention. The inventors point out that these depicted embodiments are merely a few illustrations of the many possible embodiments constructed in accordance with the basic principles of the invention disclosed herein. FIG. 1(e) is a simple SLM 120 configured as a standard round aperture 121 as a pupil. Many different sizes and shapes can be employed as can embodiments having more than one aperture. Two symmetrically oriented apertures can be used to obtain symmetric illumination beams directed onto a target and can be used to obtain symmetric collection patterns when used in a collection SLM (e.g., 112 of FIG. 1(d)). FIG. 1(f) is a simple SLM 130 configured with an annular aperture 131 as a pupil. As before, many different sizes and shapes can be employed. A symmetrically oriented annular aperture can be used to obtain symmetric illumination beams directed onto a target and can be used to obtain symmetric collection patterns when used in a collection SLM (e.g., 112 of FIG. 1(d)). Also various annular collection patterns can be used to selectively collect various diffraction orders of the scattered signal enabling a wide range of information to be collected. Additionally, as hinted at above, FIG. 1(g) discloses an SLM 140 configured with many symmetrically arranged apertures 141 that can be used top generate symmetric illumination beams and/or to collect various types of information from the scattering pattern. It is very important to note that these patterns can be quickly adjusted during testing ("on the fly") to enable highly selective and accurate metrology measurements to be made varying a variety of parameters at will. The inventors point out that the disclosed patterns here are merely descriptive and not intended to be limited to only the depicted embodiments.

Figure 2:
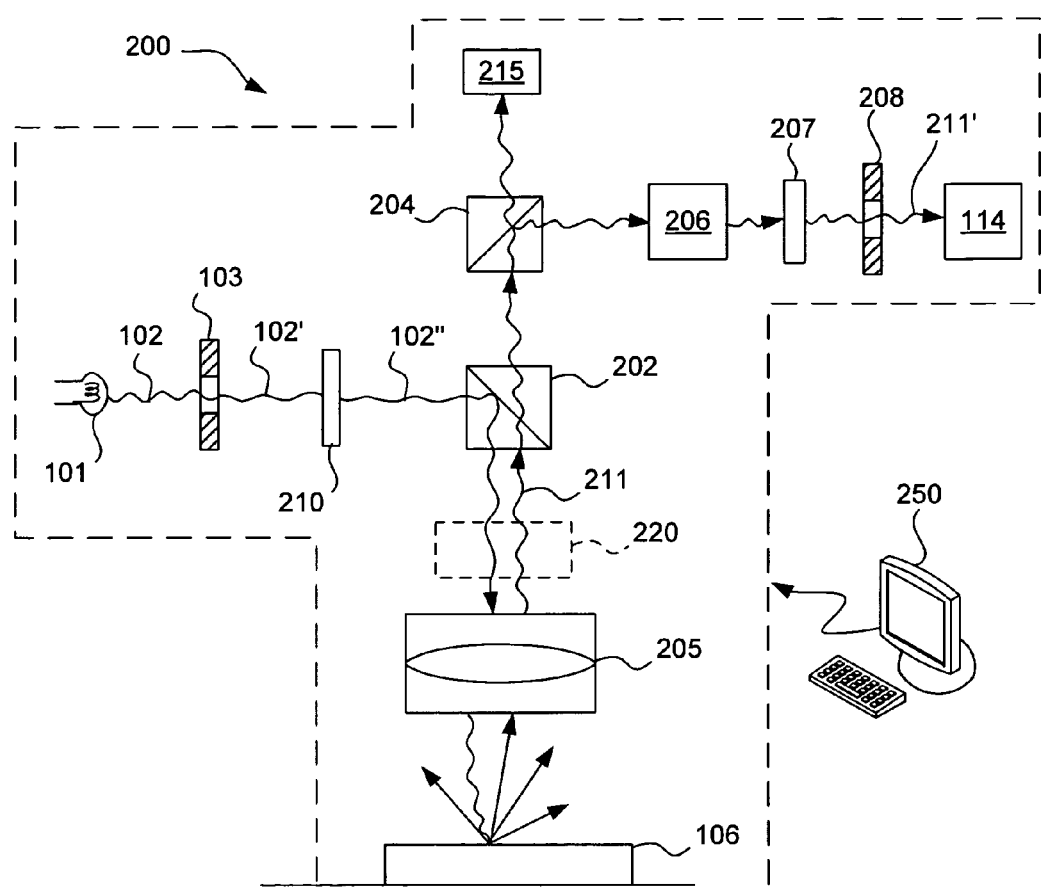
FIG. 2 depicts another simplified schematic cross-sectional view of a flexible scatterometry apparatus embodiment constructed in accordance with the principles of the invention.

FIG. 2 is another embodiment depicted in simplified schematic form. This architecture of the invention 200 which can be employed in, for example, applications requiring a lesser degree of fidelity with respect to the embodiment of FIG. 1(d). This embodiment still includes a high quality imaging system 215 and can employ extensive use of refractive optics (e.g., in the objective lens system 205).

Again, an illumination source 101 is positioned to illuminate a target 106. As before, this limited to no particular optical arrangement of any kind. In the depicted arrangement, the illumination source 101 is off to a side of the device 200. Many other arrangements are of course possible. The source 101 generates a light beam 102 which is directed through a first optical beam shaping and positioning element 103 (i.e., the illumination beam shaper) arranged in a pupil plane of the device. As before, many pupil planes can be chosen, but a back focal plane of the system is advantageous in some embodiments. As described above, this element 103 can be a rotating or sliding set of apertures of the desired patterns or apertures that can be introduced into the pupil plane. Alternatively, a fixed size pupil can be moved to various predetermined positions in the pupil plane. Also, the first optical beam shaping and positioning element 103 can be a spatial light modulator placed in the pupil plane to adjust the size, shape, and position of an aperture to adjust the spatial pattern of the light 102 passing through the modulator. Alternatively, diffractive optical elements can be used as the optical beam shaping and positioning element 103.

As before, by appropriately positioning of the center of an aperture (either the illumination aperture 103 or collection aperture 208), the AOI, angle of collection and the illumination and collection azimuth can all be selectively varied. The size of the apertures can also determine the effective illumination and collection NA's. In one example, a ring shaped aperture could be used to detect different order scattering depending on the position and radius of the collection aperture. In another example, a collection aperture 208 of a selected radius could be sized to capture zero order scattered signal only, or $1^{st}$ and $0^{th}$ order signal, or $2^{nd}$, $1^{st}$, $0^{th}$ order signal and so on.

In the depicted embodiment, the modulated incident beam 102' is directed into polarizer 210. The polarized beam 102" is directed onto a partially transparent beam splitter 202 which directs a portion of the polarized beam 102" onto the objective 205. Suitable types and embodiments for objective lens systems are known to those having ordinary skill in the art. Refractive and reflective lens systems (as well as combinations thereof) may be employed in accordance with the principles of the invention. In the depicted embodiment, an all refractive optic system can be used. In particular, the objective 205 can comprise entirely refractive optics. In another case were UV radiation is used, for example, it would be advantageous to use an entirely reflected objective lens system.

Again, the objective 205 is a large NA system (e.g., 0.90 or better, depending on the needs of the greatest NA portions of the metrology system). The beam 102" is then directed onto the target 106 where it is scattered by the topology. This scattered signal is then collected by the large NA objective lens system 205 and directed toward the receiving instrumentation 114 and relay optics 206 and through the second beam shaping element 208. In this embodiment, the received signal 211 passes upward to the partially transparent beam splitter 202. After a portion of the signal 211 passes through the first beam splitter 202 it is incident upon a second partially transparent beam splitter 204 which allows a portion of the signal 211 to pass through to an imaging or vision system 209 (generally used for navigation purposes).

Simultaneously, a portion of the signal 211 is reflected by the partially transparent beam splitter 204 into a system of relay optics 206. Commonly, such relay optics are used to make corrections for the various optical systems and generate the image of the pupil in the collection path The signal is also received by an analyzer 207. Commonly such analyzers are polarizers. Together with the polarizer 210, the analyzer 207 can be used to enable ellipsometry measurements in accordance with aspects of the invention. Passing through the analyzer 207 the signal enters another optical beam shaping and positioning element 208 arranged in a collection pupil plane of the device. As described above, this optical beam shaping and positioning element 208 can be an adjustable set of apertures configured to provide the desired aperture patterns, configurations, or positions in the pupil plane. Also, the optical modulator 208 can be a spatial light modulator arranged in the pupil plane to adjust the size, shape, and position of an aperture to adjust the spatial pattern of the light 211 passing through the modulator. Thus, as before, the adjustable pupil 208 can vary the collection NA (which may be helpful in separating out different diffraction orders among other things), collection azimuth, and collection angle. The applicants also mention here that the polarizers 207, 210 can be moved or replaced by a single polarizer located at 220. Such an embodiment will be discussed below.

Also, as before, in alternative embodiments the optical beam shaping and positioning element 208 can comprise diffractive optical elements or a spatial light modulator.

Returning to the embodiment depicted in FIG. 2, the modulated beam 211' passes through the relay optics 206, analyzer 207, optical beam shaping and positioning element 208, and onto detector devices 114 which can comprise a number of different devices. In one particularly useful embodiment, such a device comprises spectrometer 114 configured to obtain spectrographic measurements. The applicants further point out that control circuitry 250 can be connected with the device 200 and can be used to control all operational aspects of the device 200. Examples can include the control of a stage upon which a target substrate 106 can be placed, control of the beam shaping elements 103, 208, and all of the other controllable elements of the device 100 (including, but not limited to, the polarizers and analyzers 210, 220, 207, the detectors 114, 215, the movable optical elements and illumination sources and so on). Such control elements are typically microprocessor controlled and comprise a wide range of control elements known to those having ordinary skill in the art.

The inventive tools of this disclosure include several advantageous attributes including, but not limited to, the following aspects:

The tool enables the AOI and NA to be adjusted during metrology testing processes (rather than during a pre-test set up) to enable different scatterometry applications on the same tool. In a similar vein, the angle of collection can also be adjusted. Example methods of achieving such having been described previously herein.

Embodiments of the invention allow adjustable azimuth control. Thus, the inventors specifically contemplate enabling sensitivity optimization for each measurement, for example, in CD and SCOL applications. Additionally, the freely adjustable "on-the-fly" azimuth control enables the use of an R-theta stage (which may be required for integrated metrology) in CD and SCOL applications. For example, targets at different positions on the wafer generally must be measured at different azimuth angles. On-the-fly azimuth control enables compensation of this stage effect by the optical system. Thus, targets at different locations would be measured with identical scattering configurations.

The inventive architecture enables symmetric illumination and collection (by choosing symmetric apertures). For example, an SLM can be arranged to implement two symmetrically arranged apertures that enable a pair of symmetric illumination beams to be projected onto the same illumination target point. This enables 1D spectral imaging, which is can significantly improve the accuracy and MAM time of SCOL processes. This can enable scatterometric characterization of new test structures such as OPC (optical proximity correction) optimization structures, and may generally reduce the size requirements of scatterometry based metrology structures. Additionally, collection symmetry is enabled by using a similar application at the collection shaping element (e.g., 112, 208). Thus, the device is no longer required to operate using only off axis illumination.

Figure 3A:
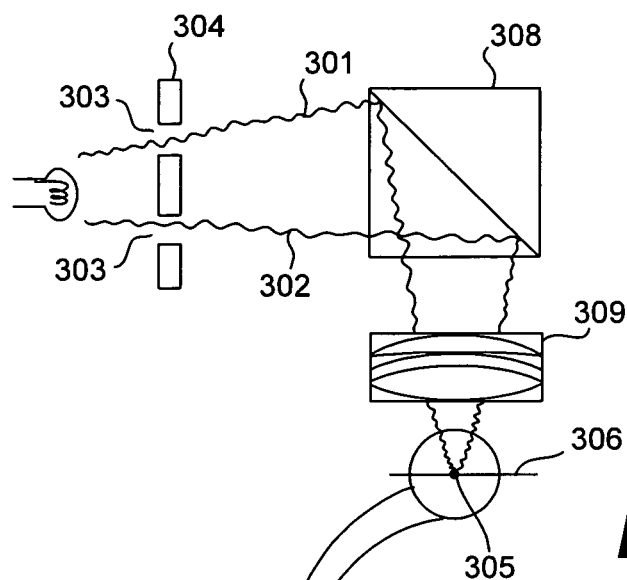
FIG. 3(a) is simplified schematic depiction of a portion of a scatterometry apparatus embodiment depicting one implementation of a symmetric illumination beam of the invention.
Figure 3B:
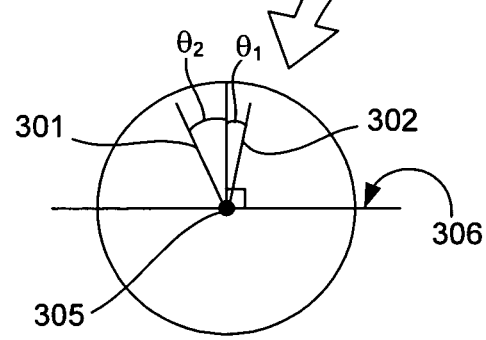
FIG. 3(b) is an expanded view of the simplified schematic of FIG. 3(a) which depicts a portion of an apparatus embodiment depicting a symmetric illumination beam in accordance with the principles of the invention.

The following illustration provided in simplified for in FIG. 3(*a*) illustrates the point. In this simplified illustration, a pair of illumination beams 301, 302 pass through a pair of apertures 303 in a beam shaping device 304 (e.g., an SLM). The beams are directed through a high NA objective 309 onto a target surface (e.g., using a beam splitter 308). The apertures 303 arranged such that the exit beams are symmetric about a spot 305 in the target plane 306.

FIG. 3(*b*) depicts schematically the symmetric nature of the illumination beams 301, 302. Such beams are defined by equal angles of incidence $\theta_1$ and $\theta_2$.

Such an architecture and beam arrangement is not possible in the prior art which requires off axis illumination and the placement of the collector in the complementary axis preventing the complementary angle from being used as an illumination origination. It can be stated that a similar symmetric collection angles can also be used. Also, the inventors contemplate that many other symmetric illumination beam configurations can be employed with the two beam configuration being merely illustrative in nature. In particular, illumination beams having multi-beam configurations with many beams or specifically characterized annular illumination beams can be employed. Other configurations are contemplated by the inventors and fall within the scope of the presently patented invention.

The inventive device architecture enables on-the-fly selection of the diffraction order of the collected light (by choosing desired pupil aperture arrangement on the collection side). This feature enables a wide range of detection algorithms and enhancing certain scatterometry applications.

Many embodiments of the invention are consistent with high quality imaging, which may be useful for combining imaging and scatterometry applications (e.g. for overlay metrology) in a very efficient way (in terms of cost, reliability and system size).

The invention enables new advantageous scatterometry applications especially applications requiring synchronized rotation of a polarizer and an analyzer (e.g. SCOL). The invention enables the use of a single rotating polarizer which plays the roles of both polarizer and analyzer, eliminating the need for synchronization. For example, referring to FIG. 2, polarizer 210 and analyzer can be removed and replaced by a single rotating polarizer position at, for example, 220. This improves the repeatability, reliability and cost of the system.

Embodiments of the invention use an objective, rather than a set of mirrors or lenses and thereby eliminating the need for repeated optical alignments at the customer site, thus improving reliability. The resulting system is also more compact, an advantage for integrated applications.

The inventive architecture is compatible with on-the-fly modification of the illumination such that the tool can operate interchangeably in bright field mode and dark field mode. This can be accomplished in many different ways. However, in one particular embodiment, such a change is accomplish by merely changing the size and shape of the second optical beam shaping and positioning elements (e.g., 112, 208). Such interchangeability adds versatility and utility to defect inspection applications.

Figure 4:
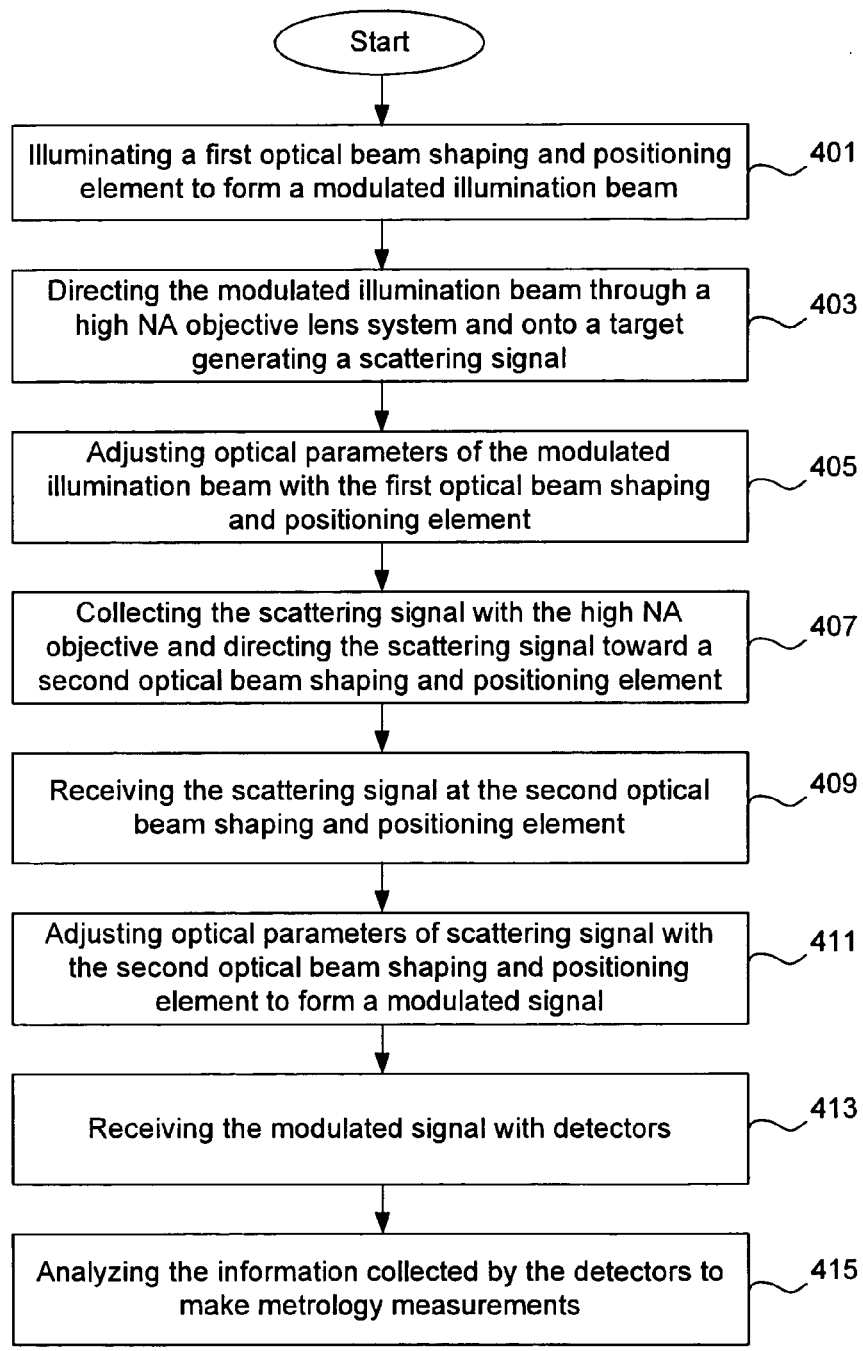
FIG. 4 is a simplified flow diagram illustrating method operations used in one method embodiment in accordance with the principles of the invention.

FIG. 4 provides a simplified expression of a methodology used to operate the devices described herein. Commonly, an inspection substrate is placed on the apparatus. Typically, the subject is a wafer or a mask which is secured to a movable chuck. The vision system of the apparatus is used to navigate to the regions of interest on the substrate. Once the appropriate target site is identified and aligned with the optical system measurements can be made.

Step 401 involves the operation of illuminating a first optical beam shaping and positioning element (e.g., 103) arranged at an illumination pupil plane P of the apparatus so that a modulated illumination beam 102' passes through the element.

Step 403 involves the operation of directing the modulated illumination beam 102' through a high numerical aperture objective lens system (e.g., 105, 205) and onto a target site where the target topology generates a light scattering signal S. The beam 102' can be acted upon by other optical elements (e.g., polarizers 210, 220, beamsplitters 202, reflectors 104a, and so on) interposed in the optical path between the first optical beam shaping element and the objective.

Step 403 is performed in conjunction with Step 401. Step 403 includes adjusting the first optical beam shaping and positioning element to adjust the optical parameters of the modulated illumination beam. This can, in some embodiments, include changing the size shape and position of apertures in the first optical beam shaping and positioning element. Where the first optical beam shaping and positioning element comprises SLM's with reflective elements it will be the reflective pattern that is adjusted so that the optical parameters of the illumination beam is altered. The idea being that, with any of the beam shaping embodiments, the angle of incidence (AOI), illumination azimuth, illumination NA, and other parameters can easily be altered using the inventive technology. As explained above with respect to Step 403, the modulated illumination beam 102' is then directed onto the target surface where it generates a scattering pattern.

In Step 407 a portion of the light scattering signal is captured using the high numerical aperture objective lens system 105, 205 which directs the scattering signal toward a second optical beam shaping and positioning element 112, 208 arranged at a collection pupil plane of the apparatus. Again optical elements can be interposed in the optical path between the illuminated target surface and the objective (e.g., polarizers 220 and so on).

The scattering signal passes through the objective and is directed along an optical path where it is received at the second optical beam shaping and positioning element (Step 409). Again, optical elements can be interposed in the optical path between the second optical beam shaping and positioning element and the objective (e.g., beam splitters 202, 204, reflectors 104b, polarizers 220, 207, relay optics 206, and so on).

In Step 411 the operation of adjusting optical parameters of scattering signal can be performed using with second optical beam shaping and positioning element to generate a modulated scattering signal. As with the previously described beam shaper, adjusting can include changing the size shape and position of apertures in the first optical beam shaping and positioning element. Where the second optical beam shaping and positioning element comprises SLM's with reflective elements it will be the reflective pattern that is adjusted so that the optical parameters of the scattering signal are altered. The idea being that, with any of the beam shaping embodiments, the angle of collection (AOC), collection azimuth, collection NA, and other parameters can easily be altered using the inventive technology. Of particular utility, are features enabling specific diffraction orders to be preferentially collected specific settings of the second optical beam shaping and positioning element. Also, of particular utility is the ability to switch between dark field and bright field imaging "on-the-fly". Also, useful is the ability to enable the collection of symmetric collection signal.

In Step 413, the modulated signal from the second optical beam shaping and positioning element is received by a detector element capable of analyzing the modulated signal. Spectrometers and numerous other detectors can be employed in this capacity.

Additionally, the data collected by the system can be used to analyze the information collected by the detectors to make metrology measurements (Step 415). Such analysis enables a wide range of metrology measurements to be made.

The present invention has been particularly shown and described with respect to certain preferred embodiments and specific features thereof. However, it should be noted that the above-described embodiments are intended to describe the principles of the invention, not limit its scope. Therefore, as is readily apparent to those of ordinary skill in the art, various changes and modifications in form and detail may be made without departing from the spirit and scope of the invention as set forth in the appended claims. Other embodiments and variations to the depicted embodiments will be apparent to those skilled in the art and may be made without departing from the spirit and scope of the invention as defined in the following claims. Further, reference in the claims to an element in the singular is not intended to mean "one and only one" unless explicitly stated, but rather, "one or more". Furthermore, the embodiments illustratively disclosed herein can be practiced without any element, which is not specifically disclosed herein.

We claim:

1. A scatterometry apparatus for enabling flexible modes of operation, the apparatus comprising in operative combination:
   an illumination source configured for emitting an illumination beam;
   a first spatial light modulator configured for receiving the illumination beam and generating a modulated illumination beam;
   at least one high numerical aperture objective lens configured for receiving both the modulated illumination beam and light reflected by a scatterometry target;
   a second spatial light modulator configured for receiving light reflected by the scatterometry target that is emitted by the at least one high numerical aperture objective lens;
   a control element electrically coupled with at least one of the first spatial light modulator and the second spatial light modulator; a detector including a spectrometer configured for generating scatterometry data from light reflected by the scatterometry target and emitted by the second spatial light modulator; and
   a computing device configured for processing the scatterometry data to compute at least one of: one or more thin film metrology characteristics of the scatterometry target, one or more critical dimension metrology characteristics of the scatterometry target, or one or more scatterometry overlay metrology characteristics of the scatterometry target.

2. The scatterometry apparatus of claim 1, wherein the first the spatial light modulator enables the adjustment of at least one of an illumination numerical aperture, an illumination azimuth, and an angle of incidence associated with the at least one illumination beam directed onto the scatterometry target; and wherein the second spatial light modulator enables the adjustment of a collection numerical aperture, a collection azimuth, and angle of collection for light reflected by the scatterometry target.

3. The scatterometry apparatus of claim 1 wherein the light emitted by the first spatial light modulator has a symmetric pattern.

4. The scatterometry apparatus of claim 1 wherein the light reflected by the scatterometry target and emitted by the second spatial light modulator is symmetric about the target site.

5. The scatterometry apparatus of claim 1 wherein the control element is configured to adjust the first spatial light modulator during the one or more metrology measurements.

6. The scatterometry apparatus of claim 1 wherein the control element is configured to alter the light received by the detector by adjusting the second spatial light modulator during the one or more metrology measurements.

7. The scatterometry apparatus of claim 1 further comprising: a first rotating polarizer element arranged in an optical path for the illumination beam; and a second rotating polarizer in an optical path for the light reflected by the scatterometry target.

8. The scatterometry apparatus of claim 1 wherein the control element enables the alteration of the mode of operation between dark field operation and light field operation by adjusting the second spatial light modulator.

9. A flexible scatterometry apparatus comprising:
   an illumination source for generating a light beam;
   a first spatial light modulator configured for receiving and modulating the light beam;
   at least one objective lens having a high numerical aperture configured for both:
      directing a light beam modulated by the spatial light modulator on to a scatterometry target to generate a scattering signal including light reflected by the scatterometry target, and
      collecting the scattering signal;
   an second spatial light modulator configured for receiving the scattering signal emitted by the at least one objective lens and modulating the signal; and
   a detector for receiving a modulated scattering signal; and
   a computing device configured for processing said modulated scattering signal to compute at least one of: one or more thin film metrology characteristics of the scatterometry target, one or more critical dimension metrology characteristics of the scatterometry target, or one or more scatterometry overlay metrology characteristics of the scatterometry target.

10. The scatterometry apparatus of claim 9,
    wherein the light beam modulated by the spatial light modulator is directed to a focal point on the scatterometry target;
    wherein the at least one objective lens includes at least one stationary objective lens disposed over the focal point on the scatterometry target;
    wherein the spatial light modulator is configured to be adjusted to alter an angle of incidence, an illumination azimuth, illumination numerical aperture, and shape associated with the light beam modulated by the spatial light modulator; and
    wherein the second spatial light modulator is configured to be adjusted to alter an angle of collection, a collection azimuth, a collection numerical aperture, and diffraction order associated with the scattering signal.

11. The scatterometry apparatus of claim 10, wherein the first spatial light modulator includes a variable aperture arrangement enabling selection of an angle of incidence, illumination azimuth, illumination numerical aperture, and shape associated with the light beam modulated by the first spatial light modulator.

12. The scatterometry apparatus of claim 10, wherein the first spatial light modulator includes a diffractive element arranged to produce a beam shaping structure in a first pupil plane enabling selection of an angle of incidence, illumination azimuth, illumination numerical aperture, and shape associated with the light beam modulated by the first spatial light modulator.

13. The scatterometry apparatus of claim 10, wherein the second spatial light modulator includes a variable aperture arrangement enabling selection of an angle of collection, a collection azimuth, a collection numerical aperture, and diffraction order associated with the scattering signal.

14. The scatterometry apparatus of claim 10, wherein the second spatial light modulator includes a diffractive element arranged to produce a beam shaping structure in a collection pupil plane enabling the selection of an angle of collection, a collection azimuth, a collection numerical aperture, and diffraction order associated with the scattering signal.

15. The scatterometry apparatus of claim 10, wherein the second spatial light modulator includes a spatial light modulator capable of altering collection parameters associated with the scattering signal.

16. The scatterometry apparatus of claim 10, wherein the second spatial light modulator is configured to selectively filter the scattering signal so that only predetermined diffraction orders of the scattering signal are received at the detector.

17. The scatterometry apparatus of claim 10, wherein the detector for receiving the modulated scattering signal includes at least one of a visual imaging system suitable for navigation, a spectrometer, and an analyzer.

18. The scatterometry apparatus of claim 10 wherein the light beam travels along an optical path between the illumination source and the at least one objective lens; and
    wherein a polarizer is interposed in the optical path of the light beam enabling polarization of the light beam.

19. The scatterometry apparatus of claim 18 wherein the polarizer is interposed in the optical path of the light beam between the spatial light modulator and the at least one objective lens.

20. The scatterometry apparatus of claim 10 wherein the wherein the first spatial light modulator having a mass of addressable pixels is adjusted so that the light beam modulated by the spatial light modulator is symmetric about the spot on the target.

21. The scatterometry apparatus of claim 10 wherein the second spatial light modulator of the apparatus enables the apparatus to operate in both light field and dark field inspection modes.

22. A method of conducting scatterometry metrology using a flexible scatterometry apparatus, the method comprising:
    illuminating a first spatial light modulator arranged at an illumination pupil plane of the apparatus;
    adjusting optical parameters of the illumination beam with the first spatial light modulator to generate a modulated illumination beam;
    directing the modulated illumination beam through at least one high numerical aperture objective lens and onto a scatterometry target to generate a light scattering signal including light reflected by the scatterometry target;
    collecting at least a portion of the light scattering signal using the at least one high numerical aperture objective lens;
    receiving the scattering signal collected by the at least one high numerical aperture objective lens at a second spatial light modulator;
    adjusting optical parameters of the scattering signal with the optical second spatial light modulator to form a modulated scattering signal;
    receiving the modulated scattering signal with a detector configured for analyzing the modulated scattering signal to generate scattering data, where the detector includes at least one spectrometer; and
    processing the scattering data to compute at least one of: one or more thin film metrology characteristics of the scatterometry target, one or more critical dimension metrology characteristics of the scatterometry target, or one or more scatterometry overlay metrology characteristics of the scatterometry target.

23. The method of claim 22, wherein adjusting optical parameters of the illumination beam includes at least one of adjusting the angle of incidence, the illumination azimuth angle, and the illumination numerical aperture with the first spatial light modulator; and
    wherein adjusting optical parameters of the scattering signal includes at least one of adjusting the angle of collection, the collection azimuth angle, and the collection numerical aperture with the second spatial light modulator.

24. The method of claim 22, wherein adjusting optical parameters of the illumination beam includes adjusting the first spatial light modulator to generate a symmetrical modulated illumination beam.

25. The method of claim 22, wherein adjusting optical parameters of the scattering signal includes adjusting the second spatial light modulator to generate a symmetrical modulated scattering signal.

26. The method of claim 22, wherein adjusting optical parameters of the scattering signal includes adjusting the second spatial light modulator to selectively pass selected diffraction orders of the scattering signal.

27. The method of claim 22, wherein adjusting optical parameters of the scattering signal includes adjusting the second spatial light modulator to selectively enable one of a dark field mode of operation or a light field mode of operation.

28. The method of claim 23,
    wherein said first spatial light modulator includes at least one adjustable illumination aperture;
    wherein the adjusting the angle of incidence includes moving the illumination aperture so that a center of the illumination aperture is offset a distance from a center of the at least one objective lens;
    wherein the adjusting the illumination azimuth angle includes moving an illumination aperture radially about the center of the at least one objective lens;
    wherein the adjusting the illumination numerical aperture includes at least one of increasing or decreasing the diameter of the illumination aperture.

29. The method of claim 23,
    wherein said second spatial light modulator includes at least one adjustable collection aperture;
    wherein adjusting the angle of collection includes moving the adjustable collection aperture so that a center of the collection aperture is offset a distance from a center of the at least one objective lens;
    wherein adjusting the collection azimuth angle includes moving the collection aperture radially about the center of the at least one objective lens;
    wherein adjusting the collection numerical aperture for the signal includes at least one of increasing or decreasing the diameter of the collection aperture.

30. The scatterometry apparatus of claim 2 wherein the control unit is configured, using electrical signals, to control both adjustment by the first spatial light modulator and adjustment by the second spatial light modulator.

31. The scatterometry apparatus of claim 1 wherein the first spatial light modulator includes an array of micromirrors, wherein the control unit, using electrical signals, is configured to control each micromirror to block at least a portion of the illumination beam at a first predetermined time and transmit at least a portion of the illumination beam at a second predetermined time to shape the at least one illumination beam.

32. The scatterometry apparatus of claim 1 wherein the first spatial light modulator is configured to at least partially simultaneously provide at least a first aperture and a second aperture to generate at least a first modulated illumination beam and a second modulated illumination beam via the first and second apertures, respectively, the first and second illumination beams having substantially equal angles of incidence.

33. The scatterometry apparatus of claim 9 further comprising a control unit coupled with at least the spatial light modulator and the optical beam shaping and positioning element, wherein:

the first spatial light modulator is configured to adjust an illumination aperture, an illumination azimuth, and an angle of incidence of the light beam;

the optical beam shaping and positioning element is configured to adjust a collection numerical aperture, a collection azimuth and an angle of collection for the scattering signal;

the first spatial light modulator includes a mass of addressable pixels; and the control unit, using electrical signals, is configured to control each light receiving element to block at least a portion of the light beam at a first predetermined time and transmit at least a portion of the light beam at a second predetermined time to shape the at least one light beam.

34. The scatterometry apparatus of claim 1, wherein the processing the scatterometry data includes:

processing the scatterometry data to compute each of: one or more critical dimension metrology characteristics of the scatterometry target, one or more thin film metrology characteristics of the scatterometry target and computing one or more critical dimension metrology characteristics of the scatterometry target.

35. The scatterometry apparatus of claim 9, wherein the processing the scatterometry data includes:

processing the scatterometry data to compute each of: one or more critical dimension metrology characteristics of the scatterometry target, one or more thin film metrology characteristics of the scatterometry target and computing one or more critical dimension metrology characteristics of the scatterometry target.

36. The method of claim 22, wherein the processing the scatterometry data includes:

processing the scatterometry data to compute each of: one or more critical dimension metrology characteristics of the scatterometry target, one or more thin film metrology characteristics of the scatterometry target and computing one or more critical dimension metrology characteristics of the scatterometry target.

* * * * *